United States Patent [19] [11] 3,948,977
Suzuki [45] Apr. 6, 1976

[54] ALKOXY ACID OR ESTER PREPARATION

[75] Inventor: Shigeto Suzuki, San Francisco, Calif.

[73] Assignee: Chevron Research Company, San Francisco, Calif.

[22] Filed: Dec. 13, 1974

[21] Appl. No.: 532,563

[52] U.S. Cl.... 260/484 R; 260/304.2; 260/410.9 R; 260/484 A; 260/494; 260/535 R; 260/535 P
[51] Int. Cl.$^2$.......................................... C07C 69/66
[58] Field of Search........ 260/484 R, 535 R, 484 A, 260/488 F, 410.9, 494

[56] References Cited
OTHER PUBLICATIONS

Falbe, *J. Carbon Monoxide in Organic Synthesis* Springer–Verlag N.Y. 1970 p. 118.

*Primary Examiner*—Lorraine A. Weinberger
*Assistant Examiner*—P. J. Killos
*Attorney, Agent, or Firm*—G. F. Magdeburger; John Stoner, Jr.; W. Keith Turner

[57] ABSTRACT

A process for producing an alkoxyacetic acid which comprises contacting carbon monoxide with formaldehyde, an alcohol, water, and a catalyst comprising hydrogen fluoride in a reaction zone and under reaction conditions effective to form an alkoxyacetic acid including a temperature between 0°C and 100°C and a carbon monoxide partial pressure between 10 and 4000 psig. By using an excess of alcohol or omitting water, alkyl alkoxy ester, i.e., alkyl alkoxyacetate, can be produced.

Also, alkyl alkoxyacetate can be produced from dialkoxymethane by reaction of dialkoxymethane with carbon monoxide using hydrogen fluoride as a catalyst.

16 Claims, No Drawings

ALKOXY ACID OR ESTER PREPARATION

BACKGROUND OF THE INVENTION

The present invention relates to the reaction of carbon monoxide with formaldehyde and an alcohol to obtain alkoxyacetic acid or ester and also to the production of alkyl alkoxy ester from an acetal.

Alkoxyacetic acids have known uses. For example, methoxy, ethoxy and butoxy glycols are useful as solvents, and they may be obtained from the corresponding alkoxyacetic acids by esterifying the alkoxyacetic acids and then reducing.

Currently alkoxy acids are usually made by the reaction of an alcohol or the sodium salt of an alcohol with chloroacetic acid.

My related application entitled "Acid Production," Ser. No. 480,894, filed June 19, 1974, discloses a process for producing hydroxyacetic acid (commonly called glycolic acid) from carbon monoxide, formaldehyde and water.

U.S. Pat. No. 2,211,625 discloses production of an alkyl glycolate by reaction of carbon monoxide, formaldehyde and an alcohol, as follows:

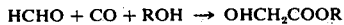

HCHO + CO + ROH → OHCH$_2$COOR

The prior art does not disclose preparation of an alkoxyacetic acid or ester from carbon monoxide, formaldehyde and an alcohol; the present invention provides a surprisingly advantageous means for such preparations.

SUMMARY OF THE INVENTION

According to a first embodiment of the present invention, a process is provided for producing an alkoxyacetic acid which comprises contacting carbon monoxide with formaldehyde, an alcohol, and a catalyst comprising hydrogen fluoride in a reaction zone and under reaction conditions effective to form an alkoxyacetic acid including a temperature between 0° and 100°C and a carbon monoxide partial pressure between 10 and 4000 psig.

Among other factors, the present invention is based on my finding that in the presence of an alcohol, an alkoxy acid product is obtained rather than, for example, a hydroxy acid product. The present invention is further based on my finding that moderate pressure and temperature are suitable for obtaining the specified products, particularly products such as alkoxyacetic acid, when using hydrogen fluoride as a catalyst.

In accordance with a second embodiment of the present invention a process is provided for producing an alkyl alkoxyacetate, i.e.,

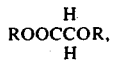

which comprises contacting carbon monoxide with formaldehyde, an alcohol, and a catalyst comprising hydrogen fluoride in a reaction zone and under reaction conditions effective to form an alkyl alkoxyacetate including a temperature between 0° and 100°C and a carbon monoxide partial pressure between 10 and 4000 psig.

In accordance with a third embodiment of the present invention a process is provided for producing an alkoxy ester, which process comprises contacting carbon monoxide with a formal (dialkoxymethane) and a catalyst comprising hydrogen fluoride in a reaction zone and under reaction conditions effective to form an alkyl alkoxyacetate including substantially anhydrous reaction conditions, a temperature between 0° and 100°C and a carbon monoxide partial pressure between 10 and 4000 psig.

The dialkoxymethane can be obtained by reacting formaldehyde with an alcohol in the presence of an acidic catalyst and, in general, using known processing techniques.

The alcohol used to produce the aforesaid formal of the third embodiment as well as the alcohol used to produce the alkoxyacetic acid or ester of the first and second embodiments of the present invention is preferably a $C_1$–$C_{20}$ primary alcohol or mixtures thereof, more preferably a $C_1$–$C_{10}$ primary alcohol or mixtures thereof, and most preferably the alcohol is methanol, ethanol, normal propanol, normal butanol, or mixtures of these $C_1$ to $C_4$ alcohols. Preferably the $C_1$–$C_{20}$ or $C_1$–$C_{10}$ group of the primary alcohol is an alkyl group.

Preferred reaction conditions for producing the alkoxyacetic acid and also for producing the alkyl alkoxyacetate directly from formaldehyde or from a formal include a temperature between 20° and 60°C and a carbon monoxide partial pressure between 10 and 3000 psig.

In producing the alkoxyacetic acid, i.e. RO—CH$_2$COOH, compounds of this invention, preferably the reactants are fed to the reaction zone at a mol percent of 3 to 35 formaldehyde; 3 to 35 alcohol; and 40 to 90 hydrogen fluoride, and the carbon monoxide partial pressure is maintained at 10 to 3000 psig in the reaction zone. If water is included in the feed, preferably 0.5 to 35 mol percent of water is in the feed.

In producing alkyl alkoxyacetates, the mol percent of the reactants fed to the reaction zone is preferably 3 to 35 formaldehyde; 3 to 35 alcohol; and 40 to 90 hydrogen fluoride, and the carbon monoxide partial pressure is maintained at 10 to 3000 psig in the reaction zone. Preferably excess alcohol is used in an amount of 1.1 to 15 mols alcohol per mol formaldehyde.

According to a further embodiment, I have found that acyloxyacetic acid is obtained by contacting carbon monoxide with formaldehyde, a carboxylic acid, and a catalyst comprising hydrogen fluoride in a reaction zone at a temperature between about 0°C and 100°C and a carbon monoxide partial pressure between 10 and 4000 psig. Thus, this embodiment is similar to the first embodiment of the present invention mentioned above except that the alcohol is replaced by a carboxylic acid. Preferably the carboxylic acid has the formula

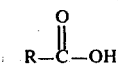

wherein R is composed of carbon and hydrogen and preferably is an alkyl group having 1 to 20 carbon atoms. Alkyl groups of 1 to 4 carbon atoms are especially preferred. The acyloxyacetic acid is useful as a solvent having both ester and acid characteristics. Also, the acyl group can by hydrolyzed off to produce the corresponding useful hydroxy acid.

EXAMPLES

EXAMPLE 1

A 300-ml magnetically stirred stainless-steel autoclave was charged with 0.30 mol of formaldehyde (trioxane), 0.33 mol of methanol, and 50 ml of hydrogen fluoride. The autoclave was next charged to 1000 psig at 10°C. The reaction mixture was stirred and allowed to warm to 34°C over a 90-minute period, during which time the pressure dropped to 710 psig. The CO pressure drop practically ceased after the initial 20 minutes. After removal of the hydrogen fluoride, analysis of the product by vapor-phase chromatography showed it to be a mixture of:
  43% methyl methoxyacetate
  42% methoxyacetic acid
  14% methyl hydroxyacetate
  1% hydroxyacetic acid This example illustrates the process of the present invention in which formaldehyde, carbon monoxide and an alcohol (methanol) are reacted in the presence of hydrogen fluoride. The product contains 85% methoxyacetic acid values which are readily realized by hydrolysis or saponification of the esters.

EXAMPLE 2

The above-described apparatus was charged with 0.20 mol of formaldehyde as paraformaldehyde, 2.0 mols of sulfuric acids, and 1.0 mol of methanol. The reactor was pressurized to 1000 psig with carbon monoxide. It was then stirred and heated at 30°C for 4 hours. The reaction mixture was diluted with water and extracted exhaustively with ether. After drying, the ether extracts were evaporated under vacuum to give a reaction product which was analyzed by vapor-phase chromatography to give:
  25% methyl methoxyacetate
  5% methoxyacetic acid
  1% methyl hydroxyacetate The above example illustrates the prior art in using sulfuric acid as the catalyst. The yields of methoxyacetic acid values are only 30%. U.S. Pat. No. 2,211,625, claiming the use of sulfuric acid in this process, reports only methyl hydroxyacetate as a product obtained in about 40% yield after 60 minutes of reaction at a relatively high temperature of 210°–220°C under the relatively high pressure of 11,700–13,200 psig (carbon monoxide pressure) (Example 1).

EXAMPLE 3

The same apparatus as used in Example 1 was charged with 0.3 mol of formaldehyde (paraformaldehyde), 0.55 mol of water and 100 ml of hydrogen fluoride. The autoclave was closed and pressurized to 2025 psig with carbon monoxide. The temperature was allowed to increase from −1°C to +22°C over a period of 70 minutes, during which time 95% of the calculated carbon monoxide pressure drop occurred within the first 10 minutes. After distilling off the hydrogen fluoride, the product was found to be over 95% hydroxyacetic acid.

This example illustrates the preparation of hydroxyacetic acid (glycolic acid) by this reaction in the presence of water and in the absence of added alcohol or other organic hydroxyl-containing substances.

EXAMPLE 4

Essentially the same procedure was followed as in Example 1, except that 0.6 mol, instead of 0.33 mol, of methanol was charged to the reactor and the reaction was carried out for 60 minutes at 27°C. The CO uptake practically ceased after 30 minutes. Analysis gave the following distribution of products:
  80% methyl methoxyacetate
  18% methoxyacetic acid
  1% hydroxyacetic acid & ester This example, as compared to Example 1, illustrates the increased yield (over 90%) in methoxyacetic acid values to be obtained by increasing the mol ratio of methanol:formaldehyde from 1.1:1 to 2:1.

EXAMPLE 5

This example was carried out the same way as Example 4, except that the 0.6 mol of methanol was replaced by 0.5 mol of ethanol and reaction time of 30 minutes. The product consisted of:
  67% ethyl ethoxyacetate
  32% ethoxyacetic acid
  1% hydroxyacetic acid & ester Similarly, runs were carried out in which the 0.5 mol of ethanol was replaced with 0.5 mol of 1-butanol and with 0.168 mol of 1-octanol (with 0.1 mol of formaldehyde in this case), respectively. The results were as follows:

| 1-Butanol Run | 1-Octanol Run |
| --- | --- |
| 66% butyl butoxyacetate | 77% octyl octyloxyacetate |
| 33% butoxyacetic acid | 5% octyloxyacetic acid |
| <1% hydroxyacetic acid & ester | <1% hydroxyacetic acid & ester |

This example illustrates the use of other alcohols in this reaction to produce the corresponding alkoxyacetic acids in good yield.

EXAMPLE 6

An experiment was carried out by essentially the same procedure as in Example 4, except that the alcohol and formaldehyde were replaced by 0.3 mol of dimethylformal, and the reaction time required was about 5 minutes. Analysis of the product gave the following:
  95% methyl methoxyacetate
  5% methoxyacetic acid This example illustrates an excellent procedure for obtaining maximum yields of alkoxyacetic acids by the process of the present invention. In this modification, dialkylformal is produced by first reacting an alcohol with formaldehyde. This is a well-known reaction. After dehydration, the dialkylformal is reacted with carbon monoxide in the presence of hydrogen fluoride to form the desired product. In the above example, dimethylformal gave a 100% yield of the methoxy derivative.

EXAMPLE 7

The apparatus of Example 1 was charged with 16 grams (0.5 mol) of methanol, 7.5 grams (0.1 mol of formaldehyde) of 40% aqueous formalin, and 50 grams of hydrogen fluoride. The autoclave was pressured to 1000 psig with carbon monoxide. The contents were stirred for 70 minutes, during which time the temperature rose from 13°C to 43°C. After cooling to room temperature and removing hydrogen fluoride, the product analyzed for:

- 90+% methyl methoxyacetate
- 5% methoxyacetic acid
- <1% methyl hydroxyacetate This example illustrates the use of formalin as a source of formaldehyde. Even with this aqueous type of feed, a good yield of methoxyacetic acid values was obtained by using a high molar ratio of methanol:formaldehyde, i.e., 5:1.

EXAMPLE 8

The same autoclave as before was charged with 0.4 mol of formaldehyde (trioxane), 0.2 mol of 1,4-butanediol and 50 grams of hydrogen fluoride. The autoclave was pressured to 1000 psig with carbon monoxide. The reaction mixture was stirred for 5 minutes, during which time the temperature rose from 18°C to 29°C. After removal of hydrogen fluoride, the crude product analyzed for the values of the following products:

- 54% 4-hydroxybutoxyacetic acid
- 18% 1,4-di(carboxymethoxy)butane
- 18% hydroxyacetic acid
- 5% diglycolic acid This example illustrates the use of a dihydric alcohol in the reaction. Each hydroxyl group functions independently, and in this example both hydroxyl groups were converted in 18% of the butanediol that was charged.

EXAMPLE 9

The autoclave was charged with 9.0 grams (0.3 mol of formaldehyde) of trioxane, 24 grams (0.33 mol) of acetic acid and 50 grams of hydrogen fluoride. The initial pressure of carbon monoxide was 1000 psig at 0°C. After 20 minutes of reaction the pressure was 620 psig and the temperature was 29°C. The product contained 86% of acetoxyacetic acid.

This example illustrates the use of the present process to produce acylacetic acid by using carboxylic acid in place of an alcohol, i.e., the R is

EXAMPLE 10

The autoclave was charged with 18.6 grams (0.30 mol) of ethylene glycol, 9.0 grams (0.30 mol formaldehyde) of trioxane and 50 ml of anhydrous hydrogen fluoride. The autoclave was then pressured to 1000 psig with CO at 24°C. The resulting mixture was stirred for 60 minutes, during which time the temperature rose to 38°C. After cooling to room temperature, the hydrogen fluoride layer was removed and the organic layer was analyzed. The crude product mixture contained:

- 10% unconverted ethylene glycol
- 80% oxoparadioxane
- 8% glycolic acid

Another run was carried out in the same way, except that 18.0 grams (0.60 mol formaldehyde) of trioxane was used. In this run, there was 100% conversion of ethylene glycol and formaldehyde. The product was over 95% yield of an equimolar mixture of oxoparadioxane and glycolic acid.

EXAMPLE 11

A 205-ml magnetically stirred copper bomb was charged with 0.2 mol of formaldehyde (as trioxane), 0.2 mol methanol, and 20 ml of hydrogen fluoride. The bomb was brought up to a pressure of only 80 psig with carbon monoxide. The reaction mixture was rapidly brought up to 50°C and stirred at 50°C for 1 hour while maintaining constant carbon monoxide pressure of 80 psig. After one hour, the copper bomb was cooled down, hydrogen fluoride was removed from the reaction mixture, and the reaction mixture was analyzed by vapor phase chromatography. The analysis showed 78% conversion of the formaldehyde feed and a selectivity to methoxyacetic acid of 90 mol percent, that is, the once-through yield of methoxyacetic acid was 70.2 mol percent.

The reaction mixture also contained a minor amount of hydroxyacetic acid, and about 22 mol percent of unreacted formaldehyde remained.

I claim:

1. A process for producing an alkoxyacetic acid which comprises contacting carbon monoxide with formaldehyde, an alcohol, and a catalyst comprising hydrogen fluoride in a reaction zone and under reaction conditions effective to form an alkoxyacetic acid including a temperature between 0° and 100°C and a carbon monoxide partial pressure between 10 and 4000 psig.

2. A process in accordance with claim 1 wherein the alcohol is a $C_1$ to $C_{20}$ primary alcohol or mixtures thereof.

3. A process in accordance with claim 2 wherein the alcohol is a $C_1$ to $C_{10}$ primary alcohol or mixtures thereof.

4. A process in accordance with claim 3 wherein the alcohol is methanol, ethanol, normal propanol, normal butanol or mixtures of these $C_1$ to $C_4$ alcohols.

5. A process in accordance with claim 1 wherein the temperature is between 20° and 60°C and the carbon monoxide partial pressure is between 10 and 3000 psig.

6. A process in accordance with claim 1 wherein the formaldehyde and alcohol are fed to the reaction zone at a mol percent of 3 to 35 formaldehyde; 3 to 35 alcohol; and 40 to 90 hydrogen fluoride; and the carbon monoxide partial pressure is maintained at 10 to 3000 psig in the reaction zone.

7. A process for producing an alkyl alkoxyacetate which comprises contacting carbon monoxide with formaldehyde, an alcohol, and a catalyst comprising hydrogen fluoride in a reaction zone and under reaction conditions effective to form an alkyl alkoxyacetate including a temperature between 0° and 100°C and a carbon monoxide partial pressure between 10 and 4000 psig.

8. A process in accordance with claim 7 wherein an excess of alcohol is used in an amount of 1.1 to 15 mols of alcohol per mol of formaldehyde.

9. A process in accordance with claim 7 wherein the alcohol is a $C_1$ to $C_{20}$ primary alcohol or mixtures thereof.

10. A process in accordance with claim 9 wherein the alcohol is a $C_1$ to $C_{10}$ primary alcohol or mixtures thereof.

11. A process in accordance with claim 10 wherein the alcohol is methanol, ethanol, normal propanol, normal butanol, or mixtures of these $C_1$ to $C_4$ alcohols.

12. A process in accordance with claim 7 wherein the temperature is between 20° and 60°C and the carbon monoxide partial pressure is between 10 and 3000 psig.

13. A process in accordance with claim 7 wherein the formaldehyde and alcohol are fed to the reaction zone at a mol percent of 3 to 35 formaldehyde; 3 to 35 alcohol; and 40 to 90 hydrogen fluoride; and the carbon monoxide partial pressure is maintained at 10 to 3000 psig in the reaction zone.

14. A process in accordance with claim 13 wherein water is also fed to the reaction zone at a mol percent of 0.5 to 35 mol percent of feed.

15. A process for producing an alkyl alkoxyacetate which comprises contacting carbon monoxide with dialkoxymethane and a catalyst comprising hydrogen fluoride in a reaction zone and under reaction conditions effective to form an alkyl alkoxyacetate including substantially anhydrous reaction conditions, a temperature between 0° and 100°C and a carbon monoxide partial pressure between 10 and 4000 psig.

16. A process for producing an acyloxyacetic acid which comprises contacting carbon monoxide with formaldehyde, a $C_2$ to $C_{21}$ carboxylic acid and a catalyst comprising hydrogen fluoride in a reaction zone at a temperature between about 0° and 100°C and a carbon monoxide partial pressure between 10 and 4000 psig.

* * * * *